United States Patent
Takagi

(10) Patent No.: US 7,424,138 B2
(45) Date of Patent: Sep. 9, 2008

(54) MEDICAL IMAGE PROCESSING APPARATUS, MEDICAL IMAGE PROCESSING SYSTEM AND MEDICAL IMAGE PROCESSING METHOD

(75) Inventor: Tatsuya Takagi, Hachioji (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 756 days.

(21) Appl. No.: 10/875,782

(22) Filed: Jun. 25, 2004

(65) Prior Publication Data
US 2005/0002551 A1    Jan. 6, 2005

(30) Foreign Application Priority Data
Jul. 1, 2003    (JP) ............................. 2003-189492

(51) Int. Cl.
*G06K 9/00* (2006.01)
(52) U.S. Cl. ...................... 382/128; 382/254; 128/922; 378/4
(58) Field of Classification Search ................ 382/100, 382/128, 129, 130, 131, 132, 209, 215, 217, 382/254, 260, 261, 262, 263, 264, 265; 128/922; 375/240.29, 343, 350; 359/308, 337.2, 339, 359/359, 498, 502, 559, 568, 588, 590, 723; 378/4–27
See application file for complete search history.

(56) References Cited

U.S. PATENT DOCUMENTS

| | | | | |
|---|---|---|---|---|
| 6,173,086 B1 * | 1/2001 | Hara | ........................... | 382/276 |
| 2003/0091243 A1 * | 5/2003 | Sasada | ........................ | 382/260 |
| 2005/0220265 A1 * | 10/2005 | Besson | ........................ | 378/16 |
| 2007/0019847 A1 * | 1/2007 | Inoue et al. | ................. | 382/128 |

FOREIGN PATENT DOCUMENTS

| | | |
|---|---|---|
| EP | 0 792 060 A1 | 8/1997 |
| EP | 0 867 835 A2 | 9/1998 |
| EP | 1 265 194 A2 | 12/2002 |
| EP | 1 505 540 A2 | 2/2005 |

OTHER PUBLICATIONS

European Search Report.
A. Baydush et al., "Improved Image Quality in Digital Mammography with Image Processing", Med. Phys. vol. 27(7), Jul. 2000, pp. 1503-1508.
M. Honda et al., "A Technique of Scatter-Glare Correction Using a Digital Filtration", Med. Phys. 20(1), Jan./Feb. 1993, pp. 59-69.

* cited by examiner

*Primary Examiner*—Anand Bhatnagar
(74) *Attorney, Agent, or Firm*—Finnegan, Henderson, Farabow, Garrett & Dunner

(57) ABSTRACT

A medical image processing apparatus which performs an image processing on a radiation image including a grid pattern obtained by performing radiography with a grid for eliminating scattered radiation, the grid being stationary and located between a subject and a detector for recording subject information, includes: a filtering section for extracting only the subject information from the radiation image by using a plurality of filters having different characteristics from each other, to eliminate the grid pattern.

12 Claims, 7 Drawing Sheets

_81_

| | AREAa | AREAb | AREAc |
|---|---|---|---|
| GRIDX | A-1 | A-2 | A-3 |
| GRIDY | B-1 | B-2 | B-3 |
| GRIDZ | A-1 | A-2 | A-4 |

FILTER TYPE
A : GABOR
B : WAVELET

FILTER CHARACTERISTIC
1 : HIGH FREQUENCY
2 : MIDDLE FREQUENCY
3 : LOW FREQUENCY

|  | AREAa | AREAb | AREAc |
|---|---|---|---|
| GRIDX | A-1 | A-2 | A-3 |
| GRIDY | B-1 | B-2 | B-3 |
| GRIDZ | A-1 | A-2 | A-4 |

FILTER TYPE  
A : GABOR  
B : WAVELET

FILTER CHARACTERISTIC  
1 : HIGH FREQUENCY  
2 : MIDDLE FREQUENCY  
3 : LOW FREQUENCY

MEDICAL IMAGE PROCESSING APPARATUS, MEDICAL IMAGE PROCESSING SYSTEM AND MEDICAL IMAGE PROCESSING METHOD

BACKGROUND OF THE INVENTION

1. Field of the Invention

The invention relates to a medical image processing apparatus, a medical image processing system and a medical image processing method for performing an image process on a radiation image radiographed with a grid, the radiation image including a grid pattern.

2. Description of Related Art

Up to now, a radiation image represented by an X-ray image has been widely used for disease diagnosis or the like. These days, as a method for obtaining the radiation image, what is proposed is a radiation image recording/regenerating method with the use of "photostimulable phosphor", which accumulates and records irradiated radiation energy, and which emits light according to the accumulated-recorded radiation energy when excitation light is irradiated thereto.

The radiation image recording/regenerating method is carried out in the following way. First, radiation which has transmitted through a subject is irradiated toward the photostimulable phosphor. Then, after radiation energy corresponding to radiation transmittance density of each part of the subject (hereafter, such radiation energy is referred to as "subject information") is accumulated and recorded in the photostimulable phosphor, excitation light stimulates the accumulated-recorded radiation energy in the photostimulable phosphor to be emitted as light. Then, intensity of the emitted light is converted into electrical signals, and the electrical signals are transformed to regenerate a visible image in image recording material such as photosensitive material or the like, or in an image display device such as a CRT or the like.

However, according to the radiation image recording/regenerating method, although there is an advantage that it is possible to obtain a radiation image having abundant information amount, with extremely low exposure dose compared to a radiography method with the use of silver halide photosensitive material, the photostimulable phosphor also accumulates and records low-energy radiation which is a result of scattering the radiation which is transmitted through the subject (scattered radiation), due to its highly sensitive characteristic. The scattered radiation may prevent from accumulating and recording subject information accurately, and thereby there is a possibility of causing various bad effects such as decrease of diagnosis efficiency.

As a way of eliminating scattered radiation, what is used is "grid", which is a laminated member covered with a cover member having low radiation absorption rate, in which radiation absorption layers made of lead or the like having high radiation absorption rate, and radiation transmittance layers made of aluminum, paper, wood, synthetic resin or the like having low radiation absorption rate are alternately laminated. The grid is located in front of the photostimulable phosphor in order to eliminate scattered radiation.

However, as described above, since the radiation absorption layers and the radiation transmittance layers are laminated alternately, a striped pattern corresponding to the grid (grid pattern) appears on the radiation image as a consequence. Based on this problem, what is known is an image processing method which is capable of eliminating moire based on an interference pattern by applying a filtering process on an original image with the use of a filter having a characteristic to eliminate the grid pattern, at the time of performing an image processing by performing multiple resolution conversion on an image including the grid pattern (see Japanese Patent Application Publication (Unexamined) No. Tokukaihei 9-44645).

Further, in a cyclical pattern suppressing method for suppressing spatial frequency component of a cyclical pattern caused from a static grid or the like, what is known is a cyclical pattern suppressing process method which is capable of obtaining a sharp, high quality image without visible appearance of a striped pattern caused from a static grid, by applying the two-dimensional wavelet transform with the use of the low-pass filter, which has a characteristic under which there is approximately no response at not less than spatial frequency corresponding to a grid pitch, for suppressing only a predetermined range adjacent to the spatial frequency component of the static grid (see Japanese Patent Application Publication (Unexamined) No. Tokukai 2001-273490).

Alternately, in the case of regenerating image data which is obtained by reading an image radiographed with a grid having different pitches, what is known is an image processing method which is capable of reducing a striped pattern caused from a grid having any pitch, from image data on which the filtering process is applied, by using a moire eliminating filter capable of reducing response of not less than 97% of spatial frequency component with respect to the special frequency component corresponding to the grid pitch, down to not more than 5% (see Japanese Patent Application Publication (Unexamined) No. Tokukai 2000-3440).

By the way, in the above-mentioned radiation image recording/regenerating method, if a normal grid having an even grid pitch is used, due to influence of an irradiation angle of a radiographing apparatus (X-ray bulb), a pitch of a grid pattern projected on a detector such as the photostimulable phosphor, an FPD or the like does not become even. For example, as shown in FIG. 7, X rays irradiated from an X-ray source 2 are transmitted through lead foils 3a and 3b of a grid 3, and then projected on an image receiving screen of a detector 4 as images 4a and 4b. Here, due to the influence of an irradiation angle of a bulb, the image 4a of the lead foil 3a is projected as a wider image than the image 4b of the lead foil 3b, which is located in a direction of primary X-ray. As a result, a grid pattern projected on the detector 4 has a characteristic of having narrow pitch at the center part but having wider pitch as the location is closer to the end part.

However, only one kind of filter is used in the conventional image processing method, which either eliminates or reduces a striped pattern caused from a grid. Therefore, for example, if a filter characteristic is determined based on image data proximate to a position perpendicular to the bulb (for example, at the center part of the detector), it is not possible to demonstrate the favorable filter characteristic around the end part where the bulb has a predetermined irradiation angle, and thereby there is a problem of decreasing performance to eliminate a grid pattern.

Further, if a focused grid is used, although an improvement can be seen on a difference of a pitch in a grid pattern between the center part and the end part, it is not possible to entirely eliminate the difference of a pitch in the grid pattern. Further, since unevenness of the pitch may occur at the grid production, and/or since unevenness of pitch may occur according to relative positions of the grid and the detector at radiography, it is difficult to eliminate a grid pattern which evenly covers the entire width of the detector.

SUMMARY OF THE INVENTION

The present invention was made in view of the problems of the above-mentioned earlier art, and an object thereof is to provide a medical image processing apparatus and a medical image processing system capable of providing a sharp radiation image having by highly accurately eliminating a grid pattern in the radiation image, the grid pattern having unevenness generated with the use of a grid, without suppressing effective high frequency component.

In accordance with a first aspect of the present invention, a medical image processing apparatus which performs an image processing on a radiation image including a grid pattern obtained by performing radiography with a grid for eliminating scattered radiation, the grid being located between a subject and a detector for recording subject information, comprises: a filtering section for extracting only the subject information from the radiation image by using a plurality of filters having different filter characteristics from each other, to eliminate the grid pattern.

In accordance with a second aspect of the present invention, a medical image processing method for performing an image processing on a radiation image including a grid pattern obtained by performing radiography with a grid for eliminating scattered radiation, the grid being located between a subject and a detector for recording subject information, comprises: extracting only the subject information from the radiation image by using a plurality of filters having different filter characteristics from each other, to eliminate the grid pattern.

According to the apparatus of the first aspect and the method of the second aspect of the present invention, if a grid pattern included in a radiation image does not have even grid pitch, it is possible to eliminate the grid pattern by applying a plurality of filters having filter characteristics according to the grid pitch. Thereby, it is possible to reliably eliminate a grid pattern included in a radiation image to precisely extract only subject information.

Preferably, in the apparatus of the first aspect of the present invention, the filtering section extracts only the subject information from the radiation image by applying one of the plurality of filters having different filter characteristics from each other, on each predetermined area of the radiation image, to eliminate the grid pattern.

Preferably, in the method of the second aspect of the present invention, the extracting comprises extracting only the subject information from the radiation image by applying one of the plurality of filters having different filter characteristics from each other, on each predetermined area of the radiation image, to eliminate the grid pattern.

According to the above-mentioned apparatus and method, if a grid pattern having uneven grid pitch according to an area of the radiation image is generated, by applying a different filter on each predetermined area, it is possible to precisely eliminate the grid pattern from the radiation image.

Preferably, in the apparatus of the first aspect and the method of the second aspect of the present invention, the plurality of filters comprise stretch and shrinkage of a waveform.

Preferably, in the apparatus of the first aspect and the method of the second aspect of the present invention, the plurality of filters comprise stretch and shrinkage of a wavelet function.

Preferably, in the apparatus of the first aspect and the method of the second aspect of the present invention, the plurality of filters comprise stretch and shrinkage of a Gabor function.

Preferably, in the apparatus of the first aspect and the method of the second aspect of the present invention, the plurality of filters comprise stretch and shrinkage of a rectangular wave.

According to the above-mentioned apparatus and method, by selecting a suitable filter according to grid characteristic and unevenness of the grid pitch, a grid pattern is precisely eliminated from a radiation image to extract only subject information. In particular, if the filter includes stretch and shrinkage the Gabor function, which has high locality, it is possible to selectively eliminate only the grid component from the radiation image. Thereby, it is possible to reduce the suppression of effective frequency component, and thereby it is possible to obtain a sharp, high quality radiation image.

Preferably, in the apparatus of the first aspect of the present invention, the filtering section extracts only the subject information from the radiation image from the radiation image by applying the plurality of filters having different filter characteristics from each other, on each of a plurality of grids having different grid densities from each other, to eliminate the grid pattern.

Preferably, in the method of the second aspect of the present invention, the extracting comprises extracting only the subject information from the radiation image from the radiation image by applying the plurality of filters having different filter characteristics from each other, on each of a plurality of grids having different grid densities from each other, to eliminate the grid pattern.

According to the above-mentioned apparatus and method, since it is possible to eliminate a grid pattern from a radiation image by applying a different filter on each grid, if there are a plurality of grids, it is possible to evenly eliminate the grid pattern by applying an optimum filter corresponding to a used grid. Thereby, it is possible to provided a high quality regenerated image.

In accordance with a third aspect of the present invention, a medical image processing system comprises: a medical image processing apparatus for performing an image processing on a radiation image including a grid pattern obtained by performing radiography with a grid for eliminating scattered radiation, the grid being located between a subject and a detector for recording subject information; and an information management apparatus for managing radiographing order information including information regarding the radiography, wherein the information management apparatus comprises: a database for storing a plurality of first filters for each grid to be applied on each predetermined area of the radiation image, the plurality of first filters having different filter characteristics from each other; a first receiving section for receiving a radiography condition including information regarding a grid to be used by the radiography; and a first transmitting section for obtaining a plurality of second filters from the database to be applied on each predetermined area of the radiation image, the plurality of second filters corresponding to the grid to be used by the radiography based on the received radiography condition, and for transmitting the obtained plurality of filters, and the medical image processing apparatus comprises: a second transmitting section for transmitting the radiography condition including the information regarding the grid to be used by the radiography; a second receiving section for receiving the plurality of second filters to be applied on each predetermined area of the radiation image, corresponding to the grid to be used by the radiography; and a filtering section for eliminating the grid pattern by applying the received plurality of second filters on each predetermined area of the radiation image and for extracting only the subject information from the radiation image.

In accordance with a fourth aspect of the present invention, a medical image processing method for a medical image radiographing system including a medical image processing apparatus for performing an image processing on a radiation image including a grid pattern obtained by performing radiography with a grid for eliminating scattered radiation, the grid being located between a subject and a detector for recording subject information; and an information management apparatus for managing radiographing order information including information regarding the radiography, comprises: storing a plurality of first filters in a database for each grid to be applied on each predetermined area of the radiation image, the plurality of first filters having different filter characteristics from each other; receiving a radiography condition including information regarding a grid to be used by the radiography; obtaining a plurality of second filters from the database to be applied on each predetermined area of the radiation image, the plurality of second filters corresponding to the grid to be used by the radiography based on the received radiography condition; transmitting the obtained plurality of second filters; transmitting the radiography condition including the information regarding the grid to be used by the radiography; receiving the plurality of second filters to be applied on each predetermined area of the radiation image, corresponding to the grid to be used by the radiography; eliminating the grid pattern by applying the received plurality of second filters on each predetermined area of the radiation image; and extracting only the subject information from the radiation image.

According to the system of the third aspect and the method of the fourth aspect of the present invention, in a medical image processing system having a structure in which a medical image processing apparatus and an information management apparatus are connected to each other through a network, the information management apparatus includes a database for storing a plurality of filters having different filter characteristics from each other for each grid to be applied on each predetermined area of the radiation image, and the medical image processing apparatus is capable of precisely eliminating the grid pattern included in the radiation image by obtaining a necessary filter from the database based on a radiography condition including information regarding a used grid. Therefore, it is not necessary to store a filter to be applied on each predetermined area of the radiation image in each medical image processing apparatus, and thereby it is possible to effectively use resources stored in the database through the network. Further, since necessary information is centralized into one place to be stored, it is possible to efficiently manage information.

BRIEF DESCRIPTION OF THE DRAWINGS

The present invention will become more fully understood from the detailed description given hereinafter and the accompanying drawing given by way of illustration only, and thus are not intended as a definition of the limits of the present invention, and wherein:

FIG. 5 is a view showing an example of a data structure of a filter selecting table 81 stored in a storing unit 8e.

EMBODIMENTS OF THE INVENTION

Hereinafter, an embodiment of the present invention will be described with reference to figures. However, the range of the present invention is not limited to the examples to be described. Here, in the present invention, it is assumed that radiation includes X rays, and a radiographing apparatus comprising an X-ray source will be described in the embodiment hereafter. However, radiation in the present invention is not specifically limited to X rays.

First, a structure of the present embodiment will be described.

Figure 1:
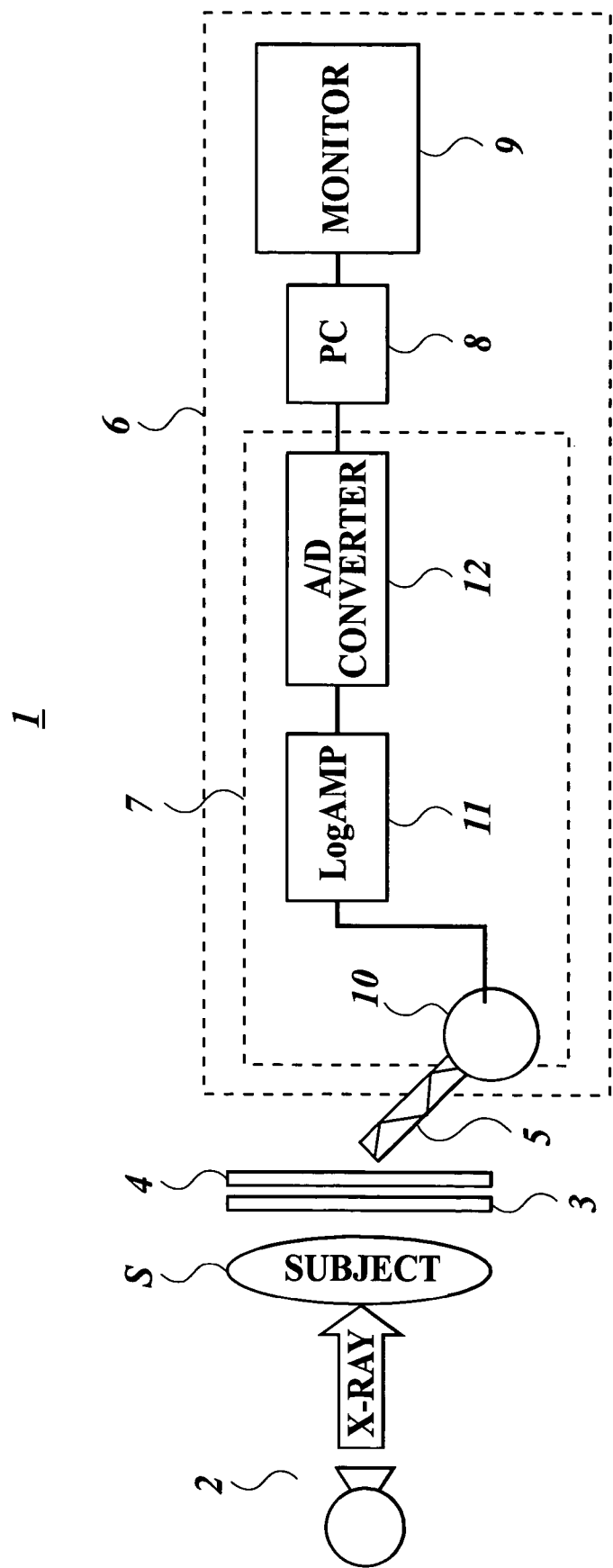
FIG. 1 is a block diagram showing a structure of a radiographing apparatus 1 according to an embodiment to which the present invention is applied.

An image processing apparatus to which the present invention is applied is, for example, used in a radiographing apparatus 1 shown in FIG. 1. The radiographing apparatus 1 comprises an X-ray source 2 for generating X rays, a grid 3 which is stationary (not movable) and which eliminates scattered radiation, a detector 4 comprising photostimulable phosphor or the like, which accumulates energy of radiation transmitted through a subject S and the grid 3, a laser light source 5 for irradiating laser light to the detector 4 to emit the energy accumulated in the photostimulable phosphor, and an image processing apparatus 6 for detecting subject information from the emitted energy to display a radiation image and to perform an image processing.

In the grid 3, radiation absorption layers and radiation transmittance layers are alternately laminated at a predetermined density, and the grid 3 faces the detector 4 so as to transmit radiation through the photostimulable phosphor. Here, a density of the radiation absorption layer and the radiation transmittance layer (grid density) is, defined as the number of pairs of respective layers per unit length, and this density is also noted as grid frequency. Here, as the grid 3, provided are a plurality of grids having different grid frequencies from each other, and depending on a radiography condition or the like, a grid having density suitable for the condition is used.

The image processing apparatus 6 comprises a radiation detecting unit 7 for sampling the energy emitted by the laser light with a predetermined sampling pitch, and for detecting digital radiation image data having therein a grid pattern, a personal computer 8 for performing an image processing based on the radiation image data obtained by the radiation detecting unit 7, and a monitor 9 for displaying an image.

The radiation detecting unit 7 comprises a photomultiplier tube 10 for sampling the energy emitted by the laser light with the predetermined frequency to be detected, and a logamp 11 for log-transforming an electric signal outputted by the photomultiplier tube 10 and for amplifying it, and an A/D converter 12 for digitally converting image information which is log-transformed by the logamp 11.

Figure 2:
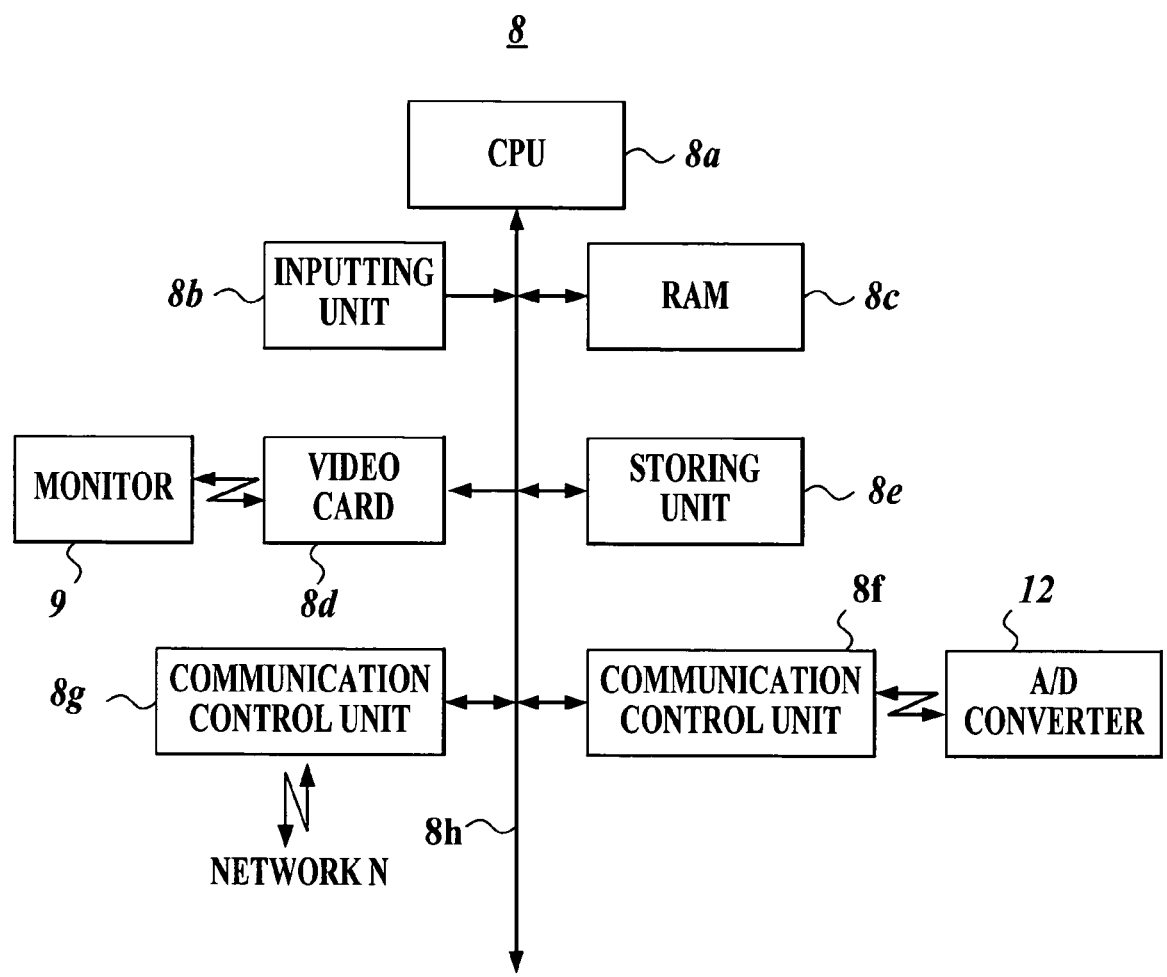
FIG. 2 is a block diagram showing an internal structure of a PC 8 shown in FIG. 1.

The personal computer 8 (hereafter, it is referred to as "PC 8") performs an image processing on a radiation image based on radiation image data which is digitally converted into by the A/D converter 12. As shown in FIG. 2, the PC 8 comprises a CPU (Central Processing Unit) 8a for centrally controlling each unit, an inputting unit 8b for accepting inputted information from an operator, a RAM (Random Access Memory) 8c for temporarily storing information, a video card 8d to which the monitor 9 is connected, a storing unit 8e for storing information, a communication control unit 8f for receiving information from the A/D converter 12, a communication control unit 8g to which a network N is connected, and a bus 8h for interconnecting the CPU 8a, the inputting unit 8b, the video card 8d, the storing unit 8e, and the communication control units 8f and 8g.

The CPU 8a develops a program assigned among various types of programs stored in the storing unit 8e, into an operation area of the RAM 8c, and performs various types of processes according to the program. Concretely, in order to eliminate a grid pattern from a radiographed radiation image, the CPU 8a performs a filter selecting process to select a plurality of filters according to a grid, and then performs a filtering process to eliminate the grid pattern from the radiation image with the use of a plurality of filters selected in the filter selecting process. Here, detail of each process will be described later.

The inputting unit 8b comprises, for example, a keyboard having a cursor key, a numeric inputting key, various types of function keys and the like, and a mouse or a tablet as a pointing device. The inputting unit 8b outputs a pushed signal according to a pushed key on the keyboard by an operator, and a positional signal of the mouse, to the CPU 8a.

The RAM 8c comprises a memory area for storing various types of data such as various types of programs, an input instruction, input data, process results and the like, so as to enable the CPU 8a to do the random access development, and the RAM 8c stores various types of states.

The storing unit 8e comprises a storage medium (not shown) in which a program, data and the like are in advance stored or can be written. This storage medium is a storage medium which is readable by the CPU 8a, such as a magnetic storage medium, an optical storage medium, a nonvolatile memory such as semiconductor or the like. The storage medium includes a medium which is fixedly provided such as a hard disk, or a detachable, removable type medium such as a CD-ROM, a memory card and the like.

In the storing unit 8e, what are stored are various types of process programs, and various types of data such as data processed by these programs, data to be processed by these programs and the like. These various types of programs include a filter selecting process program for performing the filter selecting process to select a plurality of filters according to a grid, and a filtering process program for performing the filtering process on a radiographed radiation image.

Further, in the storing unit 8e, what is stored is a filter to eliminate a grid pattern to be used when the above-mentioned filtering process program is performed. For example, in the present embodiment, as the above-mentioned filter, the Gabor filter, the wavelet filter and the like are used. Further, for each filter type, a plurality of filters having different characteristics (cut-off frequency) from each other are stored.

Further, in the storing unit 8e, in the filter selecting process, what is stored is a filter selecting table 81 for storing a plurality of filters selected for each selected area of the detector 4, for each grid. The detail of the filter selecting table 81 will be described later.

Here, a structure in which the communication control unit 8f receives a part of or all of the programs, data and the like stored in the storing unit 8e through a communication network such as LAN, WAN, Internet or the like to be stored, may be used as well. Further, the storing unit 8e may be a storage device of an external apparatus which is built on the communication network, and thereby, the various types of programs are transmitted to the external apparatus through the communication network to be installed. The RAM 8c and the storing unit 8e have a structure in which data can be erased and rewritten under the control of the CPU 8a.

The communication control unit 8f is used to communicate with an external apparatus. Here, the A/D converter 12 is connected to the communication control unit 8f under SCSI, IEEE1394, USB or the like.

The communication control unit 8g is an interface which is connectable to a transmission medium to which a network N such as LAN, WAN, Internet or the like is connected. The communication control unit 8g controls the communication with an external apparatus through a communication line such as a telephone line, ISDN line, wireless communication line, leased line, CATV line or the like.

Concretely, the communication control unit 8g controls information transmission/reception in the Hospital Information System (HIS) established within a hospital, or in the Radiology Information System (RIS) established within a department of radiology, each of which is connected through a network N.

The monitor 9 comprises a CRT (Cathode Ray Tube), an LCD (Liquid Crystal Display) or the like, and displays a screen showing various types of display data according to a display instruction inputted from the CPU 8a.

Next, a filter selecting process to select a suitable filter for each area of a radiation image obtained by X-ray radiography with the use of the grid 3 will be described, by presenting a normal grid as an example. Here, in the case of using a normal grid, since unevenness of grid pitch occurs so as to generate approximately a horizontal symmetrical appearance on a radiation image, either right half or left half from the center of the radiation image is subject to verification of filter selection. Further, it is assumed that the verification of filter selection is done based on a radiation image on which only a grid, without providing a subject, is radiographed (non-subject radiography).

Figure 3:
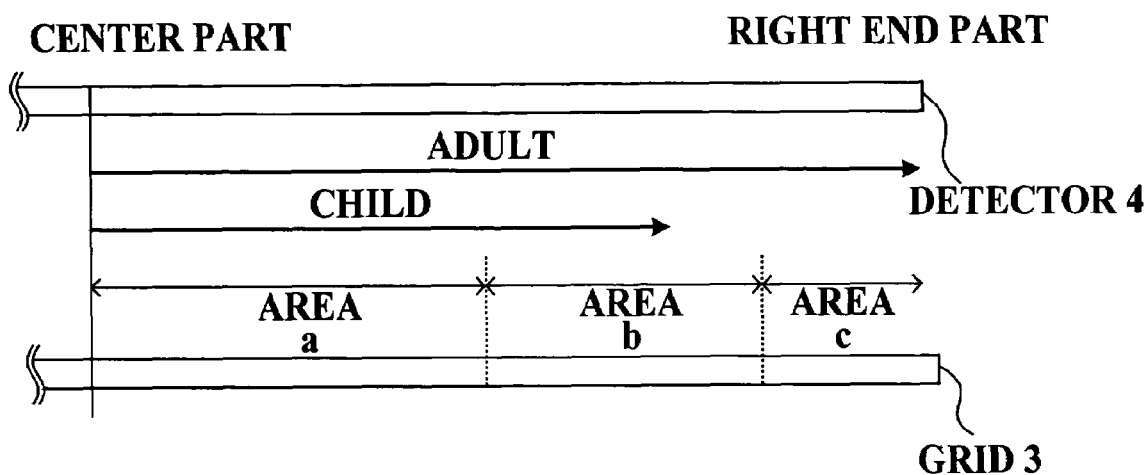
FIG. 3 is a view showing an example of dividing areas on which a filter for eliminating a grid pattern is applied.

FIG. 3 is a view showing an example of dividing a radiation image when a filter to eliminate a grid pattern from the radiation image radiographed with the use of a normal grid is to be selected according to each area of the right half of the radiation image. If a normal grid is used, while influence of the grid pitch is small around the center part, the influence becomes larger as the location is closer to the end part. Therefore, it is effective to divide areas so as to make an area of the center part large, but to make an area of the end part small. In other words, as shown in FIG. 3, a radiation image may be divided into areas so as to satisfy a relation, AREA a>AREA b>AREA c, in terms of size.

Here, the CPU 8a obtains a part of image data (for example, as much as a part occupying several lines), and performs convolution integral with a plurality of filter functions stored in the storing unit 8c. Thereby, the CPU 8a selects a filter with which an integral value is the maximum in each of AREA a to AREA c, as an optimum filter for eliminating a grid pattern. With reference to FIG. 4, selection of an optimum filter in each area will be described.

Figure 4A:
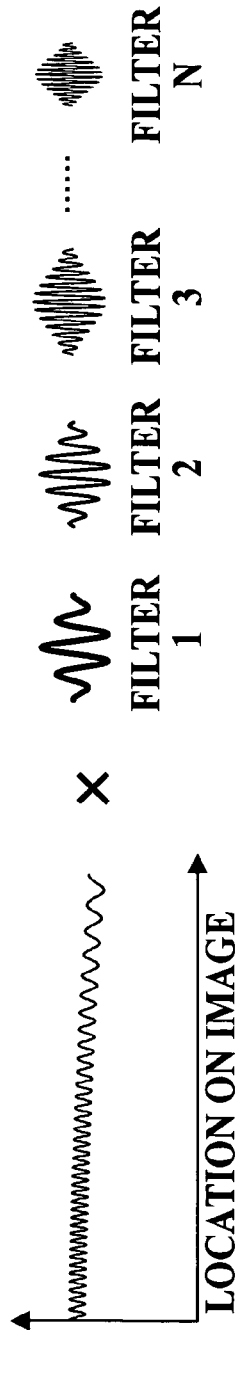
FIG. 4A is a view showing a frame format of a part of image data of a radiation image and a plurality of filters to be applied.
Figure 4B:
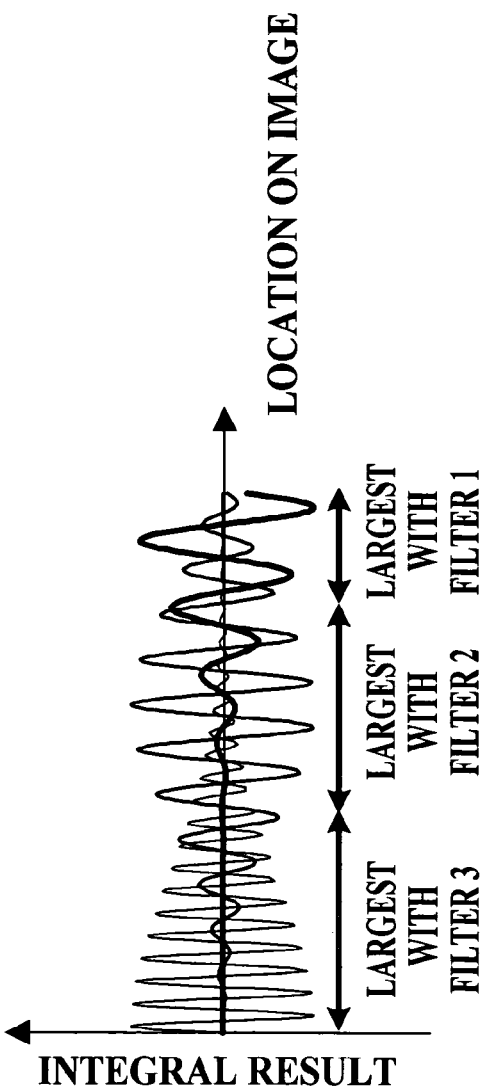
FIG. 4B is a view showing an example of a result of convolution integral which is performed for selecting an optimum filter for each divided area.

The left part of FIG. 4A is a view briefly showing image data of a part (as many as several lines) of a radiation image, and the right part of FIG. 4A is a view briefly showing filter 1 to filter N having different frequency characteristics from each other. The CPU 8a performs convolution integral on a part of image data, which is divided into AREA a to AREA c, with filter 1 to filter N, respectively, and selects a filter with which a calculated integral value is the largest as an optimum filter in each area. FIG. 4B is a view showing a result of the convolution integral with filter 1 to filter 3 in each area. An integral value is proportional to amplitude of a grid pattern detected by each filter, and the better grid is detected as the value becomes larger. Therefore, a filter having the largest integral value is selected as an optimum filter.

Further, if there are a plurality of grids having different grid densities from each other, according to the above-described method, an optimum filter in each area is selected for each grid. Here, the above-mentioned dividing example is one example in the case of using a normal grid, and therefore, depending on a type of a grid, the number of divided areas on which a filter is applied on differs, and a dividing location of the area also differs. For example, if a focused grid is used, due to influence of an X-ray tube and a radiography distance, unevenness of a grid pattern does not likely occur so as to generate a horizontal symmetrical appearance, unlike the case of a normal grid. Therefore, preferably verification of filter selection is done over the entire width of the grid. The selected filter is stored in the filter selecting table 81 so as to relate an area of each grid thereto. FIG. 5 is a view showing one example of the filter selecting table 81, created regarding GRID X to GRID Z.

In FIG. 5, "A" indicates the Gabor filter, and "B" indicates the wavelet filter. Further, "1" indicates high frequency, "2" indicates middle frequency and "3" indicates low frequency. For example, in regard to GRID X, a filter selected for AREA a is "A-1", a filter selected for AREA b is "A-2" and a filter selected for AREA c is "A-3". Accordingly, filters which are used on a radiation image radiographed with the use of GRID X are "A-3", "A-2", "A-1", "A-1", "A-2" and "A-3", in the order from the left end part. In this way, the filtering process is performed for eliminating a grid pattern from the entire radiation image.

Further, in regard to GRID Y, a filter selected for AREA a is "B-1", a filter selected for AREA b is "B-2" and a filter selected for AREA c is "B-3". Accordingly, filters which are used on a radiation image radiographed with the use of the grid X are "B-3", "B-2", "B-1", "B-1", "B-2" and "B-3", in the order from the left end part. In this way, the filtering process is performed.

Further, GRID Z is a grid which is used if a subject is a child. If a subject is a child, as shown in FIG. 3, since projection of the subject image spreads from AREA a to AREA b, a filter selected for AREA a is "A-1", and a filter selected for AREA b is "A-2". Further, a filter selected for AREA c is "A-4". Therefore, filters which are used on a radiation image radiographed with the use of the grid Z if a subject is a child are "A-4", "A-2", "A-1", "A- 1", "A-2", "A-4", in the order from the left end part. In this way, the filtering process is performed.

Next, the filtering process for eliminating a grid pattern from a radiation image with the use of a filter selected in the filter selecting process will be described. When a radiation image is inputted through the communication control unit 8f, the CPU 8a stores the inputted radiation image in the storing unit 8e. Further, the CPU 8a obtains a radiography condition (for example, a type of X-ray tube, a radiography distance, a detector characteristic, an apparatus characteristic (erect, supine, cassette), a part to be read, a grid to be used and the like) inputted at the inputting unit 8b, and stores the radiography condition in the storing unit 8e so as to relate it to the radiation image.

Continuously, the CPU 8a obtains the filter selecting table 81 from the storing unit 8e, and selects an optimum filter for each area of the radiation image based on the grid to be used, which is included in the radiography condition. Then, the CPU 8a loads the radiation image and the selected filter from the storing unit 8e and develops them into a memory area of the RAM 8c, and applies the optimum filter selected for each area on the radiation image data for performing a grid pattern elimination process.

Concretely, the grid pattern elimination process will be described by presenting the case that the selected filter is the Gabor filter, as an example. The Gabor filter is a filter function defined by the product of cosine wave which simulates a two-dimension-like grid pattern and the Gauss function. The Gabor function is a function defined by the following equation, and the detail description thereof is written in "Signal Processing and Image Processing according to Wavelet (KYORITSU SYUPPAN CO., LTD. Aug. 15, 1999)".

$$Gab(x, y) = \frac{1}{ab} e^{-\pi\left(\frac{x^2}{a^2} + \frac{y^2}{b^2}\right)} e^{2\pi j\left(\frac{x}{u} + \frac{y}{v}\right)}$$

where a, b are parameters indicating range characteristics of the wavelet, and u, v are parameters indicating period characteristics.

Figure 6:
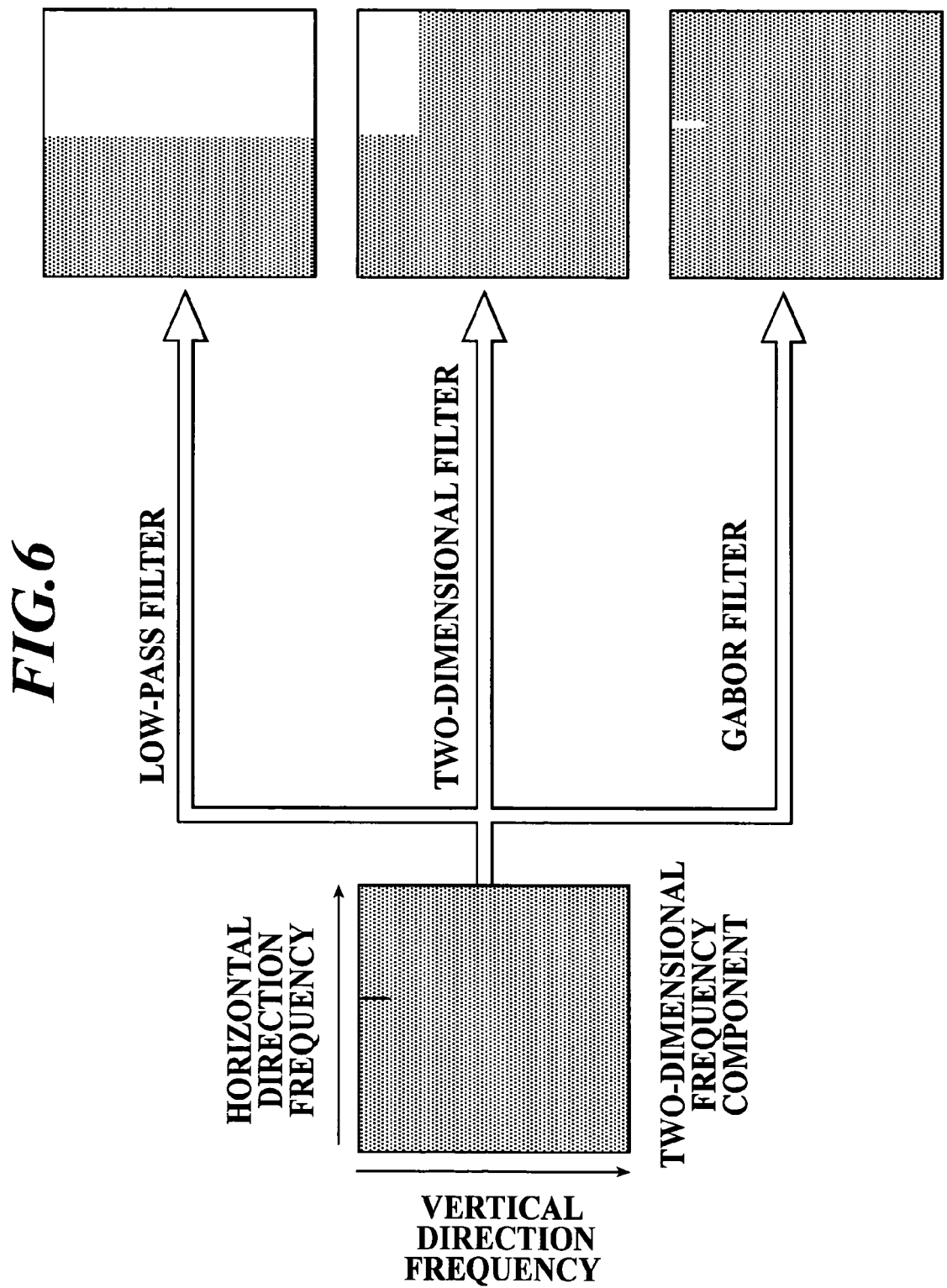
FIG. 6 is a view showing a frame format of two-dimensional frequency component after a grid pattern is eliminated with various types of filters.
Figure 7:
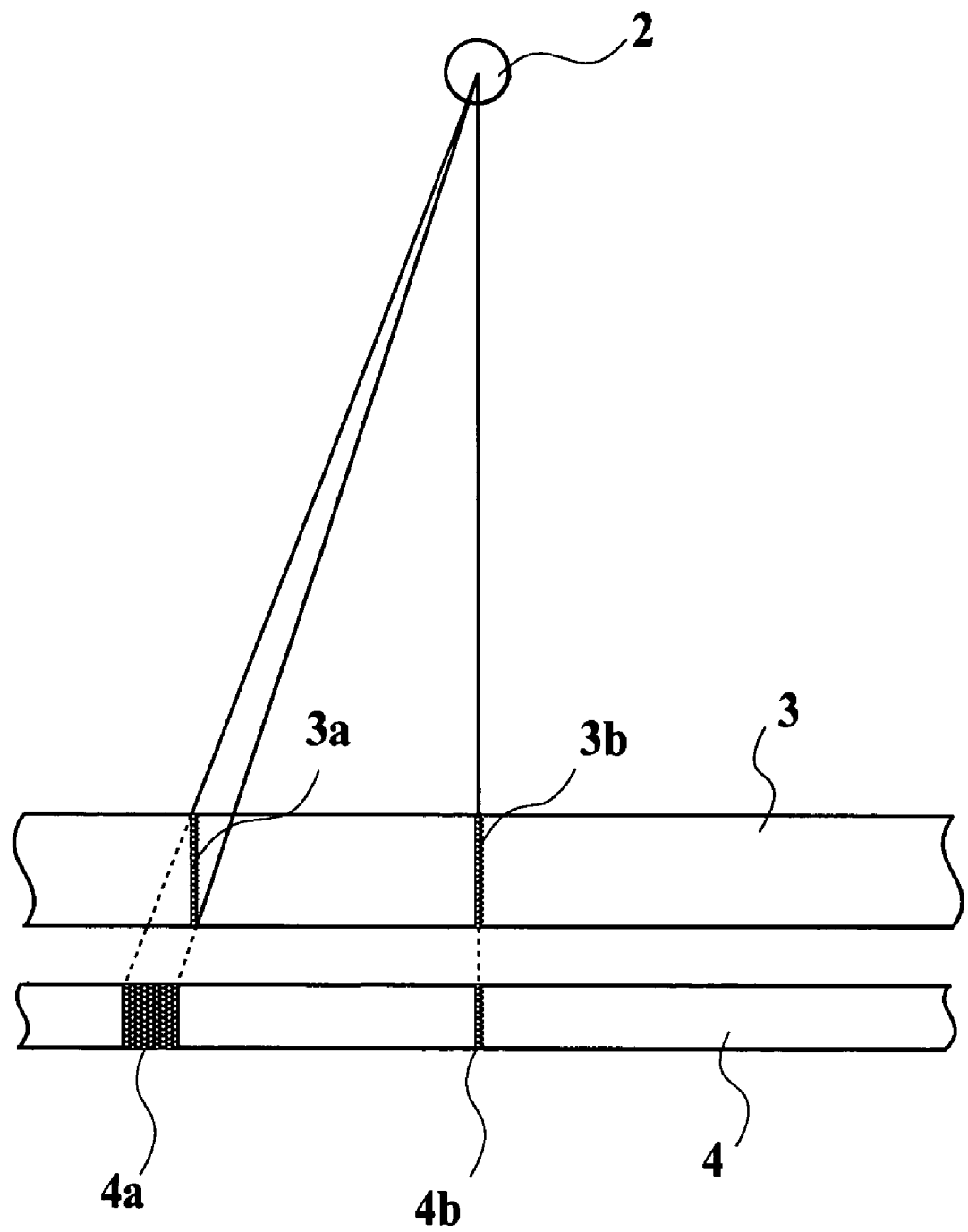
FIG. 7 is a view describing a pitch difference of a grid pattern generated with the use of a normal grid.

With reference to FIG. 6, two-dimensional frequency component suppressed in the case of eliminating a grid pattern with the Gabor filter, and the same suppressed in the case of other filters will be described. A figure shown in the left side of FIG. 6 is a view showing two-dimensional frequency component in the case that the two-dimensional Fourier transform is applied on an original image, in which grid component in a vertical direction is included. Further, figures in the right side of FIG. 6 are views showing results of performing two-dimensional Fourier transform by applying the filtering process on the original image with the low-pass filter, the two-dimensional filter and the Gabor filter, respectively. Here, for ease of description, what will be described is a case where one spot of grid component is included in the two-dimensional frequency component. However, it is assumed that the actual radiation image includes a plurality of spots of grid component.

As shown in FIG. 6, if a grid pattern is eliminated with the low-pass filter, frequency component is suppressed within a range including, horizontally a certain area from a location where the grid component is generated, and vertically a whole area. Further, if a grid pattern is eliminated with the two-dimensional filter, frequency component is suppressed within a range including, horizontally a certain area from the grid-component generated location, and vertically a certain area along a direction of height of the grid component. Further, if a grid pattern is eliminated with the Gabor filter, frequency component is suppressed within an adjacent range to the grid-component generated location.

As mentioned, if the low-pass filter or the two-dimensional filter is used, what is suppressed is not only spatial frequency component corresponding to a grid pattern, but also response of higher frequency component than the grid-corresponding spatial frequency component. As a result, what is eliminated/reduced is not only the grid pattern, but also the necessary frequency component included in the inherent image. On the other hand, if the Gabor filter, which has high locality, is used in the grid pattern elimination process, it is possible to selectively eliminate/reduce the aimed grid pattern. Thereby, it is possible to extract only necessary frequency component from a radiation image to obtain a sharp image.

As mentioned, according to the present embodiment, by applying a filter of which a characteristic (frequency characteristic) is changed according to each area, a grid pattern of which grid pitch is unevenly projected on the detector surface is eliminated in each area of a radiation image. Thereby, the grid pattern generated on the entire radiation image is reliably eliminated according to the grid pitch. Further, with the Gabor filter, it is possible to reduce the suppression of frequency component, which is suppressed at the same time of eliminating the grid pattern. Consequently, it is possible to obtain a sharp, high quality radiation image.

Here, the description in the above-mentioned embodiment is one suitable example of the radiation image processing apparatus 1 according to the present invention, and the present invention is not limited to the description. For example, in the present embodiment, what is described is the case that the radiation image processing apparatus 1 performs the above-mentioned processes in a stand-alone mode. However, the processes may be performed within the network of HIS or RIS which is connected to the radiation image processing apparatus 1 through the communication control unit 8g.

Concretely, the following structure may be applicable. The filter selecting table 81 corresponding to grids which are prepared in a radiography room is stored in a database included in an information management apparatus within the HIS or RIS, and the PC 8 transmits a radiography condition inputted at the inputting unit 8b to the information management apparatus through the network N. Then, the PC 8 obtains through the network N, a suitable filter for the grid to be used from the database of the information management apparatus, and performs the filtering process on the radiation image with the obtained filter.

According to the structure, since it is not necessary to have the filter selecting table 81 in each radiation image processing apparatus 1, it is possible to effectively use limited hardware resources. Further, by storing the filter selecting table 81 in the database, information is centralized into one place. Therefore, if there is a change or the like in the contents of the filter selecting table 81, it is possible to easily update the information, and thereby the management efficiency is improved.

Further, if the relation among the radiographing apparatus 1, the X-ray source 2 and the grid 3 is fixed, the following structure may be applicable. An apparatus ID of the radiographing apparatus 1 and a plurality of filters selected according to the grid 3 are in advance stored so as to relate each other in the database on the network N. Then, when radiography is performed by the radiographing apparatus 1, filters are selected based on the apparatus ID, and then the image processing on the radiation image radiographed by the radiographing apparatus 1 is performed.

Further, the following structure may also be applicable. Patient information, used cassette size and the like included in radiographing order information which is obtained before radiography is performed are obtained from the database of HIS or RIS, in order to determine a reading area. Alternatively, a structure in which a technician inputs information regarding a reading area for calculating an area on which the filter is applied may be also applicable.

Further, the present invention may be applied to a case of a structure in which the radiographing apparatus 1 is a portable radiographing apparatus which is movable, and a radiation image is radiographed with a cassette which incorporates therein a photostimulable phosphor sheet. In this case, in the filter selecting process, the non-subject radiography is performed for each combination of each cassette and each grid, and an optimum filter is selected for each cassette and then stored in the filter selecting table 81. Then, at the time of radiography, a radiography condition such as a radiography distance of the X-ray source 2 to a patient, a grid to be used and the like are recorded with a cassette ID as accompanying information, and when the image processing is to be performed, based on the used grid and the cassette ID, the optimum filter is obtained from the filter selecting table 81 to perform the image processing.

Thereby, it is possible to eliminate a grid pattern by applying an optimum filter according to unevenness of the grid pattern generated in each cassette, and thereby it is possible to obtain a high quality radiation image.

And so forth, needless to say, detailed structures and detailed operations of each component of the radiographing apparatus 1 in the present embodiment can be accordingly changed without departing the gist of the present invention.

According to the present invention, even if a grid pattern included in a radiation image is projected as uneven grid pitch, it is possible to eliminate the grid pattern by applying a plurality of filters having characteristics from each other according to the grid pitch. Thereby, it is possible to precisely extract only subject information by reliably eliminating the grid pattern included in the radiation image.

For example, if a normal grid is used, a plurality of filters having different characteristics from each other are respectively applied on the center part where there is small influence of the grid pitch, and on the end part where there is large influence of the grid pitch. Thereby, it is possible to reliably eliminate the grid pattern. Further, if a focused grid is used, influence of the grid pitch which is partly generated in a certain area due to fluctuation of grid production is eliminated by applying filters having different characteristics from each other on the certain area. Thereby, it is possible to appropriately eliminate the grid pattern.

Further, if a grid pattern having uneven grid pitch according to areas of a radiation image is generated, by applying a different filter on each area, it is possible to accurately eliminate the grid pattern from the radiation image.

Further, by selecting a suitable filter according to a grid characteristic, it is possible to accurately eliminate the grid pattern to extract only subject information. In particular, if a filter is stretch and shrinkage of the Gabor function, which has high locality, it is possible to selectively eliminate only grid component. Thereby, it is possible to reduce the suppression of necessary frequency component, and thereby it is possible to obtain a highly accurate, high quality radiation image.

Further, since it is possible to eliminate a grid pattern from a radiation image by applying a different filter on each grid, if there are a plurality of grids, it is possible to evenly eliminate the grid pattern by applying an optimum filter corresponding to the used grid, and thereby it is possible to provide a high quality regenerated image.

Further, in a medical image processing system which includes a medical image processing apparatus and an information management apparatus wherein the medical image processing apparatus and the information management apparatus are connected to each other through a network, the information management apparatus includes a database for storing filters for each grid, the filters having different characteristics from each other, to be applied on each area of a radiation image, and the medical image processing apparatus is capable of extracting only subject information by obtaining a necessary filter from the database based on a radiography condition including information regarding a grid to be used and of eliminating the grid pattern from the radiation image at the time of performing the image processing on the radiation image. Therefore, it is not necessary to store filters to be applied on each area of the radiation image in each medical image processing apparatus, and thereby it is possible to effectively use resources stored in the database through a network. Further, since necessary information is centralized into one place to be stored, it is possible to efficiently manage information.

The entire disclosure of a Japanese Patent Application No. Tokugan 2003-189492 filed on Jul. 1, 2003, including specifications, claims, drawings and summaries are incorporated herein by reference in their entirety.

What is claimed is:

1. A medical image processing apparatus which performs an image processing on a radiation image including a grid pattern obtained by performing radiography with a grid for eliminating scattered radiation, the grid being stationary and located between a subject and a detector for recording subject information, comprising: a filtering section for extracting only the subject information from the radiation image by using a plurality of filters having different characteristics from each other, to eliminate the grid pattern, wherein the filtering section extracts only the subject information from the radiation image by applying a suitable filter among the plurality of filters on each predetermined area of the radiation image respectively, to eliminate the grid pattern, and each predetermined area is obtained by dividing the radiation image, the predetermined areas being different from one another.

2. The apparatus of claim 1, wherein the plurality of filters comprise stretch and shrinkage of a waveform.

3. The apparatus of claim 1, wherein the plurality of filters comprise stretch and shrinkage of a wavelet function.

4. The apparatus of claim 1, wherein the plurality of filters comprise stretch and shrinkage of a Gabor function.

5. The apparatus of claim 1, wherein the plurality of filters comprise stretch and shrinkage of a rectangular wave.

6. The apparatus of claim 1, wherein the filtering section extracts only the subject information from the radiation image radiographed with one grid among different pitch sizes of grids, by applying a suitable filter in a set of filters selected among the plurality of filters according to the one grid, on each predetermined area of the radiation image respectively, to eliminate the grid pattern.

7. A medical image processing method for performing an image processing on a radiation image including a grid pattern obtained by performing radiography with a grid for eliminating scattered radiation, the grid being stationary and located between a subject and a detector for recording subject information, comprising: extracting only the subject information from the radiation image by using a plurality of filters having different characteristics from each other, to eliminate the grid pattern, wherein the extracting comprises extracting only the subject information from the radiation image by applying a suitable filter among the plurality of filters on each predetermined area of the radiation image respectively, to eliminate the grid pattern, and each predetermined area is obtained by dividing the radiation image, the predetermined areas being different from one another.

8. The method of claim 7, wherein the plurality of filters comprise stretch and shrinkage of a waveform.

9. The method of claim 7, wherein the plurality of filters comprise stretch and shrinkage of a wavelet function.

10. The method of claim 7, wherein the plurality of filters comprise stretch and shrinkage of a Gabor function.

11. The method of claim 7, wherein the plurality of filters comprise stretch and shrinkage of a rectangular wave.

12. The method of claim 7, wherein the extracting comprises extracting only the subject information from the radiation image radiographed with one grid among different pitch sizes of grids, by applying a suitable filter in a set of filters selected among the plurality of filters according to the one grid, on each predetermined area of the radiation image respectively, to eliminate the grid pattern.

* * * * *